United States Patent
Terashima et al.

(10) Patent No.: US 9,039,875 B2
(45) Date of Patent: May 26, 2015

(54) LIQUID SAMPLE MEASURING DEVICE

(71) Applicant: PANASONIC HEALTHCARE HOLDINGS CO., LTD., Minato-Ku, Tokyo (JP)

(72) Inventors: Noriyoshi Terashima, Kanagawa (JP); Teppei Shinno, Ehime (JP); Masataka Nadaoka, Ehime (JP); Yoshimasa Oda, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 8 days.

(21) Appl. No.: 13/937,225

(22) Filed: Jul. 9, 2013

(65) Prior Publication Data

US 2014/0014508 A1  Jan. 16, 2014

(30) Foreign Application Priority Data

Jul. 12, 2012  (JP) .................................. 2012-156236

(51) Int. Cl.
  *G01N 27/327* (2006.01)
  *G01N 33/487* (2006.01)
(52) U.S. Cl.
  CPC .......... *G01N 27/327* (2013.01); *G01N 27/3274* (2013.01); *G01N 33/48785* (2013.01)
(58) Field of Classification Search
  CPC ..... G01N 27/327–27/3274; C12Q 1/00–1/006
  See application file for complete search history.

(56) References Cited

U.S. PATENT DOCUMENTS

| | | |
|---|---|---|
| 2003/0159945 A1 | 8/2003 | Miyazaki et al. |
| 2006/0175206 A1 | 8/2006 | Miyazaki et al. |
| 2006/0175207 A1 | 8/2006 | Miyazaki et al. |
| 2008/0110754 A1 | 5/2008 | Miyazaki et al. |
| 2009/0205976 A1 | 8/2009 | Yoshioka et al. |
| 2010/0000880 A1 | 1/2010 | Itoh et al. |
| 2010/0252454 A1 | 10/2010 | Miyazaki et al. |
| 2010/0320097 A1 | 12/2010 | Miyazaki et al. |
| 2011/0132776 A1 | 6/2011 | Miyazaki et al. |
| 2011/0132777 A1 | 6/2011 | Miyazaki et al. |
| 2011/0257496 A1 | 10/2011 | Terashima et al. |
| 2012/0043227 A1 | 2/2012 | Miyazaki et al. |
| 2013/0020208 A1 | 1/2013 | Miyazaki et al. |

FOREIGN PATENT DOCUMENTS

| | | |
|---|---|---|
| JP | 2003-156469 A | 5/2003 |
| JP | 2011-209246 A | 10/2011 |
| WO | WO-2008/013224 A1 | 1/2008 |
| WO | WO-2008/013225 A1 | 1/2008 |
| WO | WO-2010/052849 A1 | 5/2010 |
| WO | WO-2012/132432 A1 | 10/2012 |

*Primary Examiner* — J. Christopher Ball
(74) *Attorney, Agent, or Firm* — Shinjyu Global IP

(57) ABSTRACT

The present liquid sample measuring device comprises a device body on which a biosensor is detachably mounted, a liquid biological sample being dispensed in drops on the biosensor; a measuring section that measures bioinformation from the liquid biological sample; a motion measuring section that measures motion information of the device body; a motion assessment section that assesses the degree of motion of the device body on the basis of the motion information of the device body measured by the motion measuring section; and a measurement controller that adjusts the measurement time for measuring the bioinformation on the basis of the assessment result of the motion assessment section.

9 Claims, 7 Drawing Sheets

LIQUID SAMPLE MEASURING DEVICE

CROSS-REFERENCE TO RELATED APPLICATIONS

This application claims priority under 35 U.S.C. §119 to Japanese Patent Application No. 2012-156236 filed on Jul. 12, 2012. The entire disclosure of Japanese Patent Application No. 2012-156236 is hereby incorporated herein by reference.

BACKGROUND

1. Field of the Invention

The present invention relates to a liquid sample measuring device for measuring bioinformation, such as glucose concentration or lactic acid level, from a liquid biological sample.

2. Background Art

Recently, a handheld liquid sample measuring device has been used in many settings for its capacity to carry out measurements, normally performed by a large clinical laboratory test device, in a simple manner.

Specifically, such a device has been applied, e.g., in settings where a user takes personal measurements on a daily basis at home or the like; in settings at medical facilities, such as hospitals, where a liquid sample collected by a nurse from a patient is measured in an examining room, at a bedside in a hospital ward; and the like.

This handheld liquid sample measuring device has been refined to enhance utility, and through the introduction of various measurement techniques, has gained the added values of greatly reducing the specimen quantity required for measurement and shortening the measurement time (see, e.g., Japanese Laid-open Patent Publication No. 2003-156469).

A technique has been disclosed for detecting a malfunction in such a liquid sample measuring device related to an external factor, such as in the case that the device body has suffered an impact (see, e.g., Japanese Laid-open Patent Publication No. 2011-209246).

SUMMARY

The measurement result of a handheld measuring device, for handling a liquid sample, is susceptible to inaccuracy from an impact on the device body during measurement. For this reason, the validity of a measurement result must be determined after an impact on the device.

With the device disclosed in Japanese Laid-open Patent Publication No. 2011-209246, it is determined whether an impact on the device body is to a degree that the liquid sample measuring device itself must be inspected, and bioinformation cannot be measured if the device must be inspected.

Specifically, an object of the device disclosed in Japanese Laid-open Patent Publication No. 2011-209246 is maintenance, and the validity of a measurement cannot be determined if the device body has experienced an impact while the device is measuring bioinformation.

Hence, an object of the present invention is to provide a liquid sample measuring device capable of determining whether a measurement is valid in the case that an external factor, such as an impact, has occurred during measurement of bioinformation, and modifying the measurement conditions in response to the external factor before carrying out measurement.

To achieve this object, the liquid sample measuring device of the present invention is provided with a case, a measuring section, a motion measuring section, a motion assessment section, and a measurement controller. A biosensor is detachably mounted on the case, a liquid biological sample being dispensed in drops on the biosensor. The measuring section measures bioinformation from a liquid biological sample. The motion measuring section measures motion information of the case. The motion assessment section assesses the degree of motion of the case on the basis of the motion information of the case measured by the motion measuring section. The measurement controller switches from a first condition used during normal measurement to a second condition differing from the first condition, and measures the bioinformation, on the basis of the assessment result of the motion assessment section during measurement of bioinformation by the measuring section.

Effects

The liquid sample measuring device of the present invention can determine whether a measurement is valid when the case has moved during measurement of bioinformation, and modify the measurement conditions on the basis of the degree of motion of the case.

Thus, the present invention can provide a liquid sample measuring device that determines the validity of a measurement with respect to an external factor such as impact, and has improved tolerance for external factors in comparison with the prior art.

DETAILED DESCRIPTION OF THE INVENTION

An embodiment of the liquid sample measuring device of the present invention will be described in detail hereinafter with reference to the appended drawings. It will be apparent to those skilled in the art from this disclosure that the following descriptions of the embodiments are provided for illustration only and not for the purpose of limiting the invention as defined by the appended claims and their equivalents.

Embodiment 1

Figure 1A:
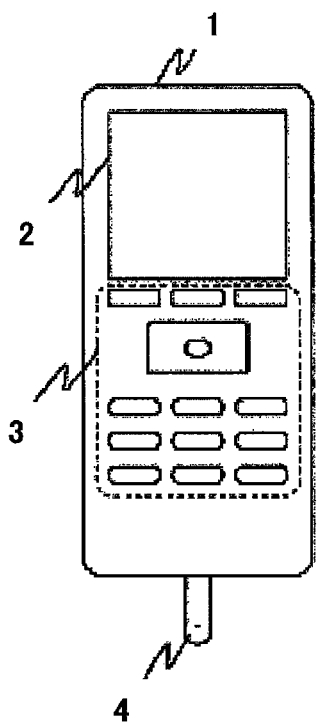
FIG. 1A is an outline diagram and FIG. 1B is a block diagram showing the configuration of the liquid sample measuring device according to an embodiment of the present invention.
Figure 1B:
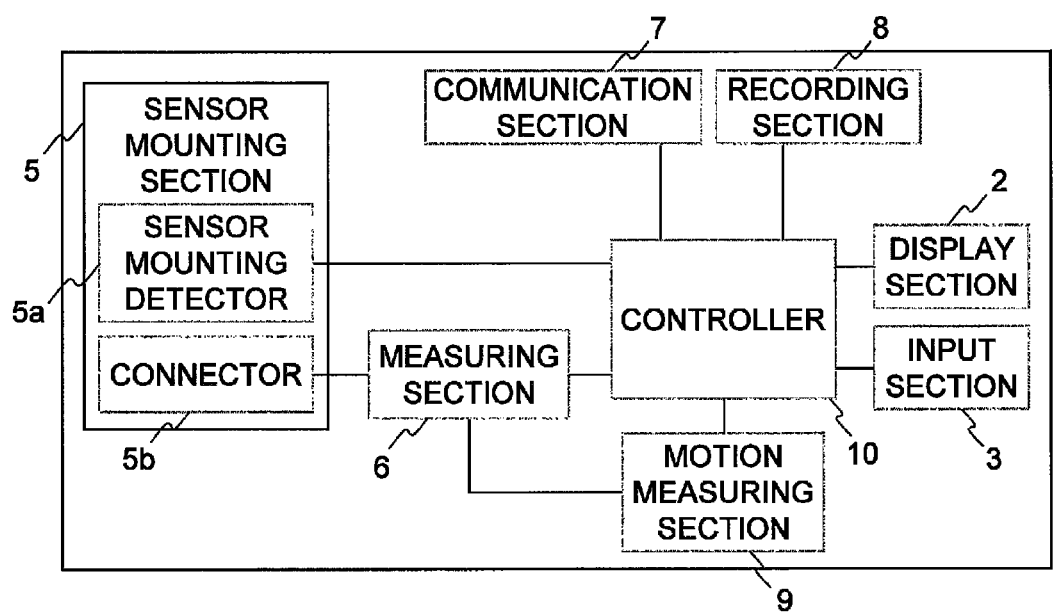

FIGS. 1A and 1B are diagrams showing the configuration of the liquid sample measuring device. FIG. 1A is an outline diagram, and FIG. 1B is a block diagram.

As shown in FIGS. 1A and 1B, the liquid sample measuring device is a handheld measuring device provided with a device body (case) 1, a display section 2, and an input section 3. A disposable biosensor 4 is mounted detachably in the device body 1.

The device body 1 is formed in a compact shape which a user, such as a nurse or a patient, can hold in one hand.

Figure 2:
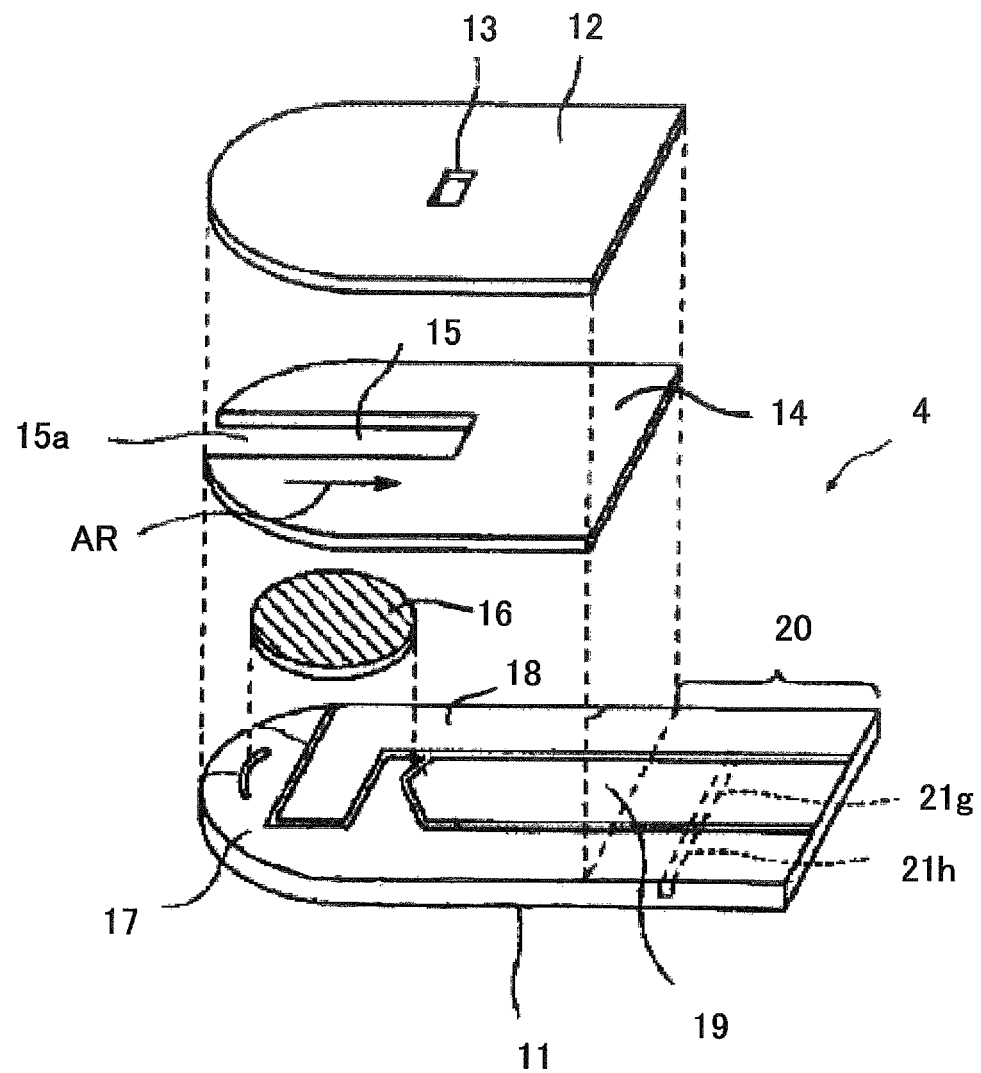
FIG. 2 is an exploded perspective view of a biosensor mounted on the liquid sample measuring device of FIG. 1.

The disposable biosensor mounted in the liquid sample measuring device is described using FIG. 2. FIG. 2 is an exploded perspective view of the biosensor 4 mounted in the device body 1.

As shown in FIG. 2, the biosensor 4 has insulating substrates 11 and 12, a spacer 14, a reagent layer 16, and the like.

The insulating substrate 11 (hereafter called simply "substrate 11") is formed from polyethylene terephthalate or the like. A conductive layer comprising an electrically conductive substance such as a metal, a precious metal such as palladium, or carbon is formed on the surface of the substrate 11 by screen printing or sputtering deposition. The conductive layer may be formed over all, or a portion of the substrate 11.

The insulating substrate 12 is arranged so as to cover a portion of the upper surface of the substrate 11, with the spacer 14 disposed in between insulating substrate 12 and substrate 11, and has an air hole 13 disposed in the center. A spacer 14 having a notched portion is placed between and combined with the substrate 11 and the substrate 12 to comprise the biosensor 4.

The conductive layer is divided by slits to form a counter electrode 17, a measurement electrode 18, and a detection electrode 19 on the substrate 11. The electrodes 17, 18, and 19 may be formed on at least a portion of the substrate 11, and each electrode may be connected to the device body 1 by a lead wire.

The spacer 14 is arranged so as to cover the counter electrode 17, the measurement electrode 18, and the detection electrode 19 on the substrate 11. A rectangular notched portion is disposed in the center of the front edge of the spacer 14. The notched portion constitutes a sample supply path 15.

The sample supply path 15, formed in the spacer 14, draws a sample liquid dispensed in drops on a sample dropping area 15a, the sample dropping area disposed toward the air hole 13 in the substrate 12 (in the direction of arrow AR in FIG. 2), by capillary action.

A reagent layer 16 is exposed by the notched portion of the spacer 14, and is disposed so as to cover the counter electrode 17, the measurement electrode 18, and the detection electrode 19.

The reagent layer contains oxidoreductase and an electron acceptor. These dissolve in a sample solution (in the case of the present embodiment, blood drawn from a human) drawn via the sample supply path 15, and produce a reaction. After the reaction has ended, the reduced electron acceptor is electrochemically oxidized, and the glucose concentration in the sample solution is measured from the resulting current. This series of reactions is detected by a current associated with electrochemical change read by the counter electrode 17, the measurement electrode 18, and the detection electrode 19.

A discriminating section 20 descriminates the type of the biosensor 4 and/or differences in the output characteristics of each manufacturing lot. A slit 21g and a slit 21h are formed and combined in the portions corresponding to the discriminating section 20 in the counter electrode 17 and the detection electrode 19. Thus, the device body 1 can discriminate differences in the electrical output characteristics of each biosensor 4.

The counter electrode 17, the measurement electrode 18, the counter electrode 17, and the detection electrode 19 are placed in the sample supply path 15 of the biosensor 4 along the sample flow direction (arrow AR) from the sample dropping area 15a in this order. The arrangement of the counter electrode 17 and the measurement electrode 18 may be reversed.

A predetermined gap is disposed between the measurement electrode 18 and the detection electrode 19 along the sample flow direction. Thus, the device body 1 can discriminate whether a sample solution has been drawn securely and in sufficient quantity by using the current value of the detection electrode 19.

Returning to FIGS. 1A and 1B, the components of the liquid sample measuring device will be described. FIG. 1B shows a block diagram of the liquid sample measuring device.

As shown in FIG. 1B, the liquid sample measuring device of the present embodiment comprises the display section 2, the input section 3, a sensor mounting section 5, a measuring section 6, a communication section 7, a recording section 8, a motion measuring section 9, and a controller 10 in the device body 1.

The display section 2 is directed by the controller 10 to display a glucose concentration measured by the measuring section 6, various information for a user, and the like.

The input section 3 is a device to which the user inputs movement directives, identification numbers, and the like, for which, e.g., a button disposed on the device body 1 or an optical reader such as a barcode reader may be used. Alternately, the input section 3 may receive wireless communication such as RF-ID or an input using voice recognition, or may be a touch panel which is superimposed on the display section 2 and can accept touch input instead of a button. A combination of these several input devices is used in the present embodiment. The information inputted in the input section 3 is transmitted to the controller 10.

A connector 5b electrically connected to the counter electrode 17, the measurement electrode 18, and the detection electrode 19 of the biosensor 4, as well as a sensor mounting detector 5a for detecting that the biosensor 4 is mounted in the sensor mounting section 5 are disposed inside the sensor mounting section 5.

The sensor mounting detector 5a detects that the biosensor 4 is mounted and transmits this information to the controller 10. The detection means may be, e.g., a mechanical electric switch capable of detecting a mounted object by the electric switch being pressed to become conductive while an object is mounted. Otherwise, any means that can detect the presence of an object in the mounting section, such as an optical sensor, may be used. The means may be configured so as to monitor whether an electrical connection is established between an electrode disposed in the biosensor 4 and the connector 5b to detect that the biosensor 4 is mounted when an electrical connection has been established.

The measuring section 6 is directed by the controller 10 to measure bioinformation from a liquid biological sample dispensed in drops on the biosensor 4. For example, in the case that blood has been dispensed in drops on the biosensor 4, a voltage or a current is applied through the connector 5b to each of the electrodes of the biosensor 4, and the glucose concentration in the blood is measured from the level of the current or voltage obtained in response. A switch (not shown) is disposed on the connector 5b, and can apply a voltage or a current selectively to the counter electrode 17, the measurement electrode 18, and the detection electrode 19 of the biosensor 4.

The communication section 7 is directed by the controller 10 to exchange data with another device, such as a server or a personal computer through a communication line. The communication section 7 transmits to the other device, e.g., a glucose concentration measured by the measuring section 6, motion information measured by the motion measuring section 9, or an identification number inputted to the input section 3, and receives, e.g., a list of identification numbers from the other device. The "communication line" in this description indicates a standard communication line of a mode connected wirelessly or wired to a public line, or a mode connected wirelessly or wired and one-to-one to another device.

The recording section 8 receives and records measurement results outputted by the measuring section 6, motion information outputted by the motion measuring section 9, information inputted by the input section 3, information received by the communication section 7, and the like, through the controller 10. The controller 10 controls recording and playback of data to and from the recording section 8.

The motion measuring section 9 is directed by the controller 10 to measure the degree of motion of the device body 1 for output to the controller 10 as motion information.

The controller 10 exercises overall control of the device body 1. The controller 10 issues indications to the measuring section 6, the display section 2, and the communication section 7 on the basis of information inputted by the sensor mounting detector 5a, the measuring section 6, the motion measuring section 9, and the input section 3.

When starting measurement, first, a user uses the input section 3 to input the ID of the user who is performing the measurement (a nurse), the ID of the patient who will be measured, and the ID of the biosensor 4. The user may input these ID by pressing a button on the input section 3, or in the case that the input section 3 has a barcode reader, by reading the barcode associated with each ID. Completion of input of these ID completes preparation for measurement.

Next, upon completion of preparation for measurement, the user mounts the biosensor 4.

Once mounted, the sensor mounting detector 5a detects the fact that the biosensor 4 is mounted in the sensor mounting section 5 and transmits a signal indicating this to the controller 10. Thereupon, the controller 10 directs the measuring section 6 to start measurement. As a result, the measuring section 6 measures glucose concentration by a method to be described later, and notifies the controller 10 of the measurement.

The controller 10 directs the display section 2 to display the glucose concentration measured by the measuring section 6. At the same time, candidate information associated with the measured glucose concentration is displayed, which the user may select using the input section 3.

This "candidate information" is, e.g., information related to meals, such as before or after meals, and will be used to ascertain conditions during measurement when the glucose concentration measurement result is checked later. The user can set in advance whether any candidates can be selected. Besides selecting candidate information, the user may use the input section 3 to input an arbitrary text string or the like.

Upon completion of input by the user, the controller 10 records the ID of the measurer, the ID of the subject measured, the ID of the biosensor 4, the time of measurement, the glucose concentration measurement result, the associated information indicated by the user, and the motion information outputted by the motion measuring section 9 as a group of associated data in the recording section 8. These associated data will be referred to as "measurement control data" hereafter.

During this procedure, the controller 10 monitors the measured glucose concentration, and adds an abnormal value flag to the measurement control data in the case that the glucose concentration is an abnormal concentration; an abnormal concentration is a concentration which could not normally be measured, or is outside a range indicated by the user. In the case that the abnormal value flag has been added, the controller 10 notifies the user by displaying that an abnormal value has been detected on the display section 2.

The description thus far has taken an example of a case when the liquid sample measuring device is used in an environment such as a hospital, where many measurers measure many subjects. In other words, in such an environment, the information of which biosensor was used to measure whose glucose concentration must be associated to control glucose concentration measurement results. Therefore, the ID of the user, the ID of the patient, and the ID of the biosensor 4 are inputted into the device.

Inputting the ID of the user and the ID of the patient may be omitted, however, in the case that the liquid sample measuring device has a simple configuration and limited functions, and glucose concentration measurement results for only one person will be collected. Inputting the ID of the biosensor 4 may also be omitted in the case that the ID of the biosensor 4 can be recognized by the liquid sample measuring device by reading the information of the discriminating section 20 of the biosensor 4; alternatively, the ID of the biosensor 4 itself need not be read.

The controller 10 has an internal clock (not shown). Therefore, the controller 10 uses the time indicated by the clock to carry out various control operations. Time information is also transmitted to, and used by, the measurement controller to be described later.

The motion measuring section 9 will now be described in detail. A three-dimensional acceleration sensor disposed in the device body 1, e.g., may be used for the motion measuring section 9. The number of acceleration sensors may be one or a plurality. A gyro sensor or the like may be used instead of an acceleration sensor. Any type of sensor may be used provided that it can detect change in orientation relative to the direction of gravity and motion of the device body 1.

Figure 3A:
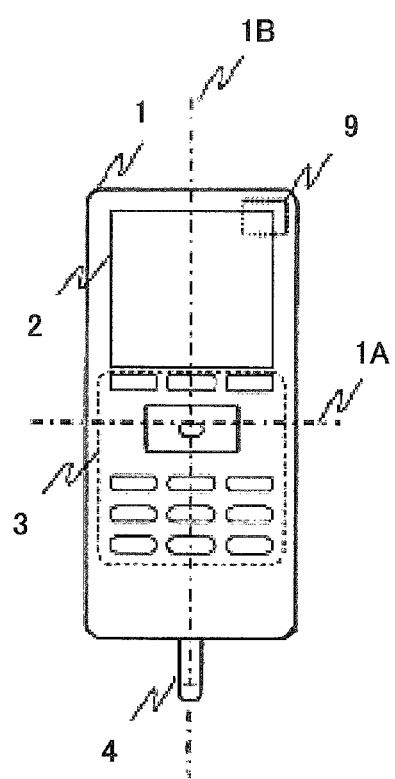
FIGS. 3A and 3B are diagrams showing an example of the motion measuring section contained in the liquid sample measuring device of FIG. 1.

FIG. 3A shows an example in which one acceleration sensor is disposed in the device body 1 as the motion measuring section 9. The acceleration sensor is arranged in a position offset from the centerline (1A, 1B) and on the opposite side of the device body 1 from the side on which the biosensor 4 is mounted. This position is also offset from the center of gravity of the weight of the device body 1.

This arrangement allows the motion measuring section 9 to detect the orientation and motion of the biosensor 4 with good precision. This is especially effective for monitoring the position of a liquid sample or the like, because the sample dispensed in drops on the biosensor 4 is a liquid and the spreading and position of the liquid changes depending on the orientation and motion of the biosensor 4, which risks influencing the glucose concentration measurement result.

Figure 3B:
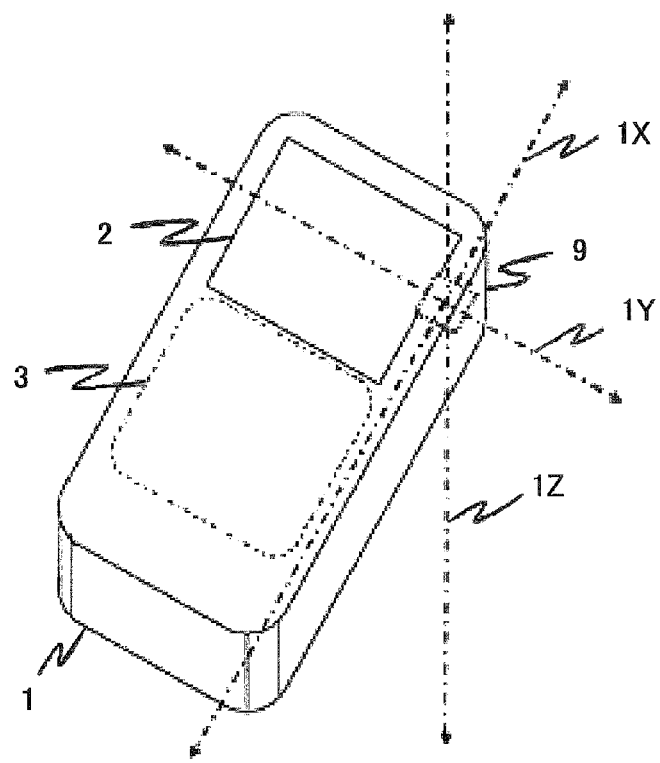

FIG. 3B shows three-dimensional axes layered over a schematic view of the device body 1. The longer direction relative to the device body 1 is the x-axis 1X, the shorter direction is the y-axis 1Y, and the height direction is the z-axis 1Z. The acceleration sensor arranged as the motion measuring section 9 is an all-purpose sensor for detecting variation per unit time along each of these three-dimensional axes.

The type of sensor is not limited to an acceleration sensor, provided that the sensor can detect such variation.

While directed by the controller 10, the motion measuring section 9 outputs variation per unit time along each of the detected three-dimensional axes to the measuring section 6 as motion information. Variation may be expressed numerically as an absolute value or a relative value, and need only contain as much information as is needed to be able to reproduce the motion of the device body 1 on the basis of this motion information. Similarly, a suitable interval over which the motion of the device body 1 can be reproduced is selected for the interval over which this motion information is outputted, i.e., the sampling interval.

Figure 4:
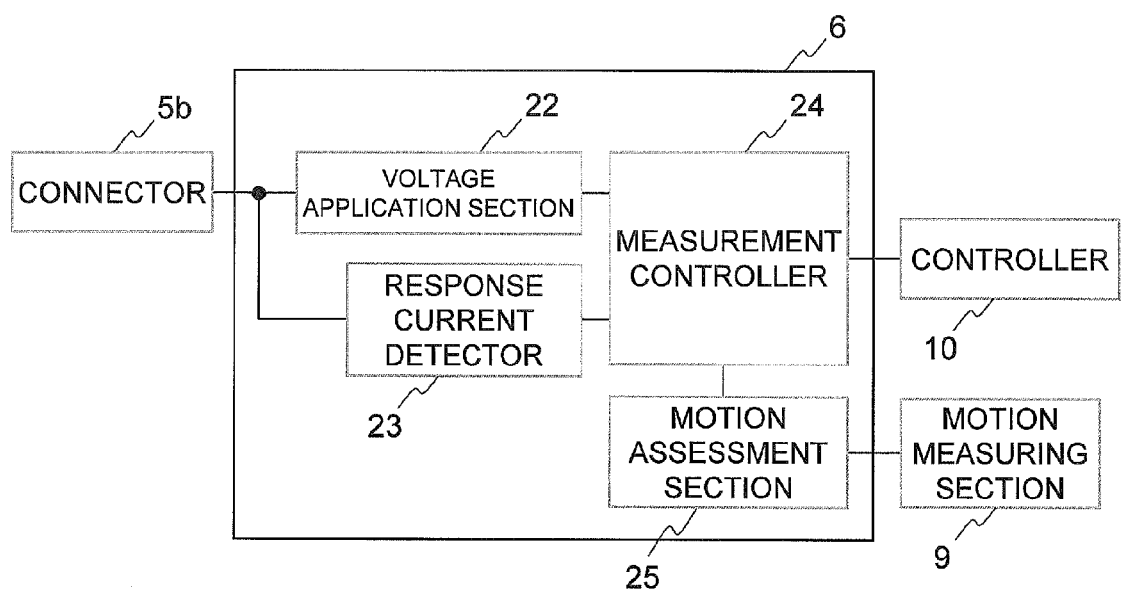
FIG. 4 is a block diagram of the measuring section contained in the liquid sample measuring device of FIG. 1.

Next, the configuration and operation of the measuring section 6 will be described using FIG. 4. FIG. 4 is a block diagram showing the internal configuration of the measuring section 6 and connections to peripheral sections.

As shown in FIG. 4, the measuring section 6 has a voltage application section 22 connected to the connector 5b; a response current detector 23; a measurement controller 24 connected between the voltage application section 22, the response current detector 23, and the controller 10 to control measurement of glucose concentration; and a motion assessment section 25 for receiving motion information outputted by the motion measuring section 9 and assessing motion.

The voltage application section 22 applies a voltage to the connector 5b at a timing, interval, and voltage level as directed by the measurement controller 24.

The response current detector 23 detects change of current between the electrodes of the biosensor 4 appearing on the connector 5b, and outputs this change to the measurement controller 24. Specifically, the response current detector 23 samples the current flowing through the connector 5b over a predetermined interval, and outputs this current to the measurement controller 24 as the response current. The predetermined sampling interval is an interval from several to several tens of milliseconds for detecting change in the response current.

The voltage application section 22 and the response current detector 23, grouped together, constitute an electrical circuit or an integrated circuit, which is designed to receive the voltage application indication of the measurement controller 24 and output the response current to the measurement controller 24.

Although an example of performing a measurement on the basis of applying a voltage was described in the present embodiment, the invention may be similarly embodied using a system of measuring glucose concentration according to the level of a response voltage on the basis of applying a current.

Figure 5A:
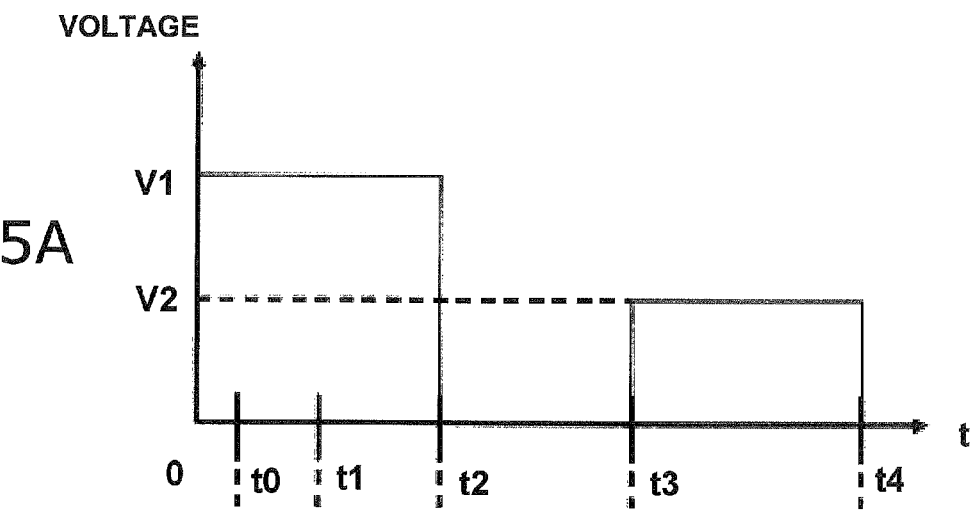
FIGS. 5A and 5B are diagrams showing the state of the application voltage and the response current during measurement by the liquid sample measuring device of FIG. 1.
Figure 5B:
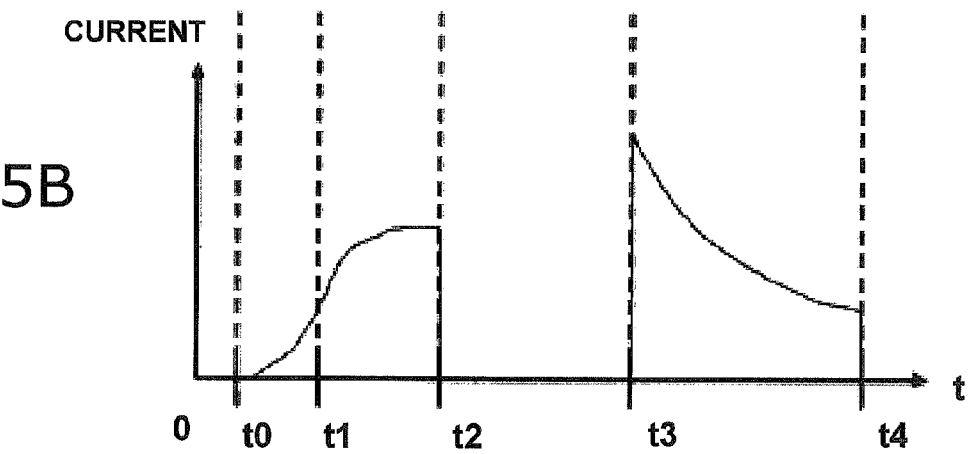

An example of the operation for measuring glucose concentration will be described using FIGS. 5A and 5B. FIG. 5A is a diagram showing the state of the voltage applied to the connector 5b, and FIG. 5B is a diagram showing the state of the response current obtained from the connector 5b. The horizontal axis in FIGS. 5A and 5B indicates time, taking as the starting point the time when the controller 10 detects that the biosensor 4 has been mounted and directs the measuring section 6 to start measuring. The vertical axis of FIG. 5A indicates the level of the voltage applied to the connector 5b, and the vertical axis of FIG. 5B indicates the response current appearing in the connector 5b.

Upon being directed by the controller 10 to start measurement, the measurement controller 24 directs the voltage application section 22 to start applying a voltage to the counter electrode 17, the measurement electrode 18, and the detection electrode 19 of the biosensor 4 through the connector 5b (time 0). At this point, no blood has been dispensed in drops on the sample dropping area 15a of the biosensor 4.

When blood is dispensed in drops in the sample dropping area 15a by the user (time t0), the blood is drawn into the sample supply path 15 by capillary action, and spreads in the direction of the air hole 13. After the spread blood has reached the counter electrode 17, the measurement electrode 18, or the detection electrode 19, whichever electrode is closest to the sample dropping area 15a, the response current starts to change.

The measurement controller 24 can detect that blood has been dispensed in drops at the time when the response current obtained from the response current detector 23 becomes greater than a predetermined value (time t1). The measurement controller 24 stores the time t1 at which dropwise dispensing was detected as the sample dropping time.

The measurement controller 24 stops applying the voltage at a time t2 when a predetermined time has elapsed since the time t1 at which the dropwise dispensing of blood was detected. The time from time 0 to time t2 is called the first potential interval.

Besides the object of detecting that blood was dispensed in drops, the object of the first potential interval is to remove interfering substances occurring when the reagent of the biosensor 4, and the sample dissolved and reacted. The voltage level (V1) of the first potential interval and an application period from time t1 to time t2 of the application time of the first potential interval are determined in advance so as to allow suitable removal of one or a plurality of interfering substances.

In response to the recent demand for shortening measurement time, the application time of the first potential interval is set to the shortest time at which no effect is presumed to be produced by external disturbance during measurement.

Next, after the first potential interval has ended, the measurement controller 24 stops applying a voltage for a predetermined interval (from time t2 to time t3). In other words, the voltage applied to the connector 5b becomes zero. The interval from time t2 to time t3 is called the waiting interval.

The waiting interval is set to encourage an enzymatic reaction in the reagent layer 16 of the biosensor 4. Although differing depending on the type and quantity of the reaction reagent used in the reagent layer 16 and the volume of the sample solution received by the sample supply path 15, this waiting interval is fixed at a predetermined time to the extent that the same type of biosensor 4 is used. Depending on the type of the reagent, a voltage may be applied during the waiting interval to encourage an enzymatic reaction.

After the waiting interval has ended, the measurement controller 24 applies a voltage at a voltage level V2 for a predetermined interval (from time t3 to time t4). This interval from time t3 to time t4 is called the second potential interval.

The second potential interval is an interval for encouraging oxidation in the reagent layer 16 of the biosensor 4, and acquiring the response current associated with measuring the final glucose concentration. Although differing depending on the type and quantity of the reaction reagent used in the reagent layer 16, and the volume of the sample solution received by the sample supply path 15, this second potential interval is fixed at a predetermined time to the extent that the same type of biosensor 4 is used.

At least one additional waiting interval may be set during the second potential interval. The application voltages during the first and second potential intervals are not constant, and may be varied. These voltages are determined by the device using an algorithm for measuring glucose concentration.

The measurement controller 24 acquires the response current associated with electrochemical change at least once during the second potential interval, and stores this current as a current profile. A glucose concentration is specified on the basis of the stored current profile using the Cottrell equation or another algorithm, and is outputted to the controller 10 as the measurement result. The controller 10 takes the time when the measuring section 6 transmitted the measured glucose concentration to be the time when measurement took place (measurement time).

The motion assessment section 25 receives motion information outputted by the motion measuring section 9, assesses the motion information, and outputs the assessment result to the measurement controller 24. The measurement controller 24 determines whether to modify the operation to measure glucose concentration on the basis of the assessment result of the motion assessment section 25.

The motion assessment section 25 periodically compares the size of variation per unit time outputted by the motion measuring section 9 for each of the three-dimensional axes with two thresholds, and makes an assessment by classifying in three categories of a first state, a second state, and a third state. First, the variation is compared in size with the first threshold for each of the three-dimensional axes. In the case that the variation is greater than the first threshold, the variation is compared in size with the second threshold, which is made larger than the first threshold.

In the case that the result is that the variation is larger than the second threshold for at least one axis, the third state is assessed. In the case that there is no axis for which the variation is greater than the second threshold, but the variation is greater than the first threshold for at least one axis, the second state is assessed. In the case that the variation is less than the first threshold for all of the three-dimensional axes, the first state is assessed.

The motion assessment section 25 periodically outputs this assessment result to the measurement controller 24. The motion assessment section 25 carries out this assessment constantly while the device body 1 is connected to power and is operating. Alternately, at the very least, this assessment is carried out from the time that insertion of the biosensor 4 has been detected until measurement of glucose concentration is completed. The assessment interval is optimally the same as the sampling interval for detecting the response current, which is an interval from several to several tens of milliseconds.

The measurement controller 24 has a memory (not shown) which is large enough to store current responses and assessment results, during at least one glucose concentration measurement cycle, to allow reference to the history of current responses inputted by the response current detector 23 and assessment results inputted by the motion assessment section 25.

The measurement controller 24 completes measurement without modifying the length of the first potential interval, the waiting interval, the second potential interval, and the level of the application voltage during the measurement of glucose concentration; if as described earlier in the case, the assessment result transmitted by the motion assessment section 25 is always the first state, from the time that insertion of the biosensor 4 is detected, until measurement of glucose concentration is completed. In other words, from time 0 to time t4 as illustrated in FIGS. 5A and 5B.

This means that the motion of the device body 1 is not great enough to influence measurement of glucose concentration, and measurement can be carried out stably.

In the case that the assessment result of the motion assessment section 25 during the specific interval from time 0 to time t4 in FIGS. 5A and 5B indicates the third state, the measurement controller 24 stops measurement of glucose concentration to issue a measurement error, or issues the same measurement error even after measurement is completed and gives some sort of measurement. In this case, upon being transmitted the measurement error by the measuring section 6, the controller 10 displays a message on the display section 2 stating that a measurement error has occurred and urging that the biosensor 4 be replaced and blood dispensed in drops again.

This means that the motion of the device body 1 is abnormal enough to greatly influence measurement of glucose concentration, and measurement is consequently impossible or risks indicating an erroneous measurement.

In the case that the assessment result of the motion assessment section 25 during the specific interval from time 0 to time t4 in FIGS. 5A and 5B indicates the second state, and indicates the third state during an interval differing from the interval described earlier during which a measurement error is issued, the measurement controller 24 makes an adjustment as to whether to modify the length of voltage application and the voltage level.

This means that the motion of the device body 1 has some influence on measurement of glucose concentration, but adjusting to refine this measurement can give a correct measurement result.

Next, the measurement operation considering the motion assessment result in the measurement controller 24 will be described using the flowchart of FIG. 6.

Step S01 is a step during which insertion of the biosensor 4 is detected and the controller 10 directs the measuring section 6 to measure glucose concentration. The measurement controller 24 directs the voltage application section 22 to start applying a voltage of the voltage level V1 to the connector 5b, and the voltage application section 22 promptly starts voltage application (time 0).

Step S02 is a step during which the measurement controller 24 detects that blood has been dispensed in drops from the change in the response current outputted by the response current detector 23 after a user has dispensed blood in drops on the sample dropping area 15a of the biosensor 4 (time t1).

Step S03 is a step during which the measurement controller 24 confirms at time t1 whether the assessment result outputted by the motion assessment section 25 during the interval from time 0 to time t1 includes an assessment of the second or third state. In the case that an assessment of the second or third state has been included at least once, the procedure moves to step S04. In the case that such an assessment has not been included once, the procedure moves to step S05 without modifying the voltage level V1 and time t2.

In step S04, the measurement controller 24 modifies the voltage level V1 currently applied by the voltage application section 22, and modifies the time t2 at which voltage application is scheduled to stop.

This is to handle the possibility that the device body 1 is in a state of being moved during the time before and after blood has been dispensed in drops on the sample dropping area 15a of the biosensor 4, and if the procedure continues, the spreading speed of the blood when spreading in the sample supply path 15 will slow and/or the volume of blood reaching the reagent will deviate, causing the blood and the reagent to dissolve unevenly and resulting in insufficient removal of interfering substances.

An example of such modification control of the application voltage level is to control voltage level V1 and time t2 by modifying voltage V1 and time t2, while keeping a constant relationship between the voltage level V1 and time t2 in which changes to either are inversely proportional to the other.

Specifically, the voltage level V1 is reduced and time t2 is lengthened (delayed). In this case, the product of the length of time from time t1 to time t2 before modifying and the voltage level V1 before modifying is the same as the product of the length of time from time t1 to time t2 after modifying and the voltage level V1 after modifying. In other words, in the case that the voltage level V1 is halved, e.g., time t2 is delayed so as to double the length of time from time t1 to time t2.

This is an effective control in the case that the degree of removal of interfering substances during the first potential interval changes proportionally to the voltage level and the application time. Thus, adequate control can be exercised without requiring excessive voltage application while assuring enough time for even dissolution, even in the case that the time that the blood and the reagent take to dissolve in the sample supply path 15 of the biosensor 4 is uneven due to the motion of the device body 1.

Another example of this modification control is to lengthen the application time (delay time t2) without modifying the voltage level V1. This is effective in the case that the degree of removal of interfering substances during the first potential interval depends only on the voltage application time. Thus, adequate control can be exercised without requiring excessive voltage application, while assuring enough time for even dissolution, even in the case that the time that the blood and the reagent take to dissolve in the sample supply path 15 of the biosensor 4 is uneven due to the motion of the device body 1.

Step S05 is a step during which the initially set time t2 or, in the case that time t2 was modified in step S04, the modified time t2 is reached. The measurement controller 24 then directs the voltage application section 22 to stop voltage application, and the voltage application section 22 promptly stops applying a voltage to the connector 5b.

Step S06 is a step during which the measurement controller 24 confirms at time t2 whether the assessment result outputted by the motion assessment section 25 during the interval from time t1 to time t2 includes an assessment of the third state. In the case that an assessment of the third state has been included at least once, the procedure moves to step SE1. In the case that such an assessment has not been included once, the procedure moves to step S07.

Step S07 is a step during which the measurement controller 24 confirms at time t2 whether the assessment result outputted by the motion assessment section 25 during the interval from time t1 to time t2 includes an assessment of the second state. In the case that an assessment of the second state has been included at least once, the procedure moves to step S08. In the case that such an assessment has not been included once, the procedure moves to step S09 without modifying time t3.

In step S08, the measurement controller 24 then modifies the time t3 at which the voltage application section 22 is scheduled to restart voltage application.

This is to handle the possibility that the device body 1 is in a state of being moved, and if the procedure continues, the enzymatic reaction occurring in the sample supply path 15 of the biosensor 4 will be blocked, delaying the reaction. Delaying time t3 at this stage to lengthen the waiting interval from time t2 to time t3 allows sufficient enzymatic reaction to occur.

Step S09 is a step during which the initially set time t3 or, in the case that time t3 was modified in step S08, the modified time t3 is reached. The measurement controller 24 then directs the voltage application section 22 to restart voltage application, and the voltage application section 22 promptly restarts applying a voltage to the connector 5b.

Step S10 is a step during which the measurement controller 24 confirms at time t3 whether the assessment result outputted by the motion assessment section 25 during the interval from time t2 to time t3 includes an assessment of the third state. In the case that an assessment of the third state has been included at least once, the procedure moves to step SE1. In the case that such an assessment has not been included once, the procedure moves to step S11.

Step S11 is a step during which the measurement controller 24 confirms at time t3 whether the assessment result outputted by the motion assessment section 25 during the interval from time t2 to time t3 includes an assessment of the second state. In the case that an assessment of the second state has been included at least once, the procedure moves to step S12. In the case that such an assessment has not been included once, the procedure moves to step S13 without modifying time t4.

In step S12, the measurement controller 24 modifies the time t4 at which the voltage application section 22 is scheduled to end voltage application. This is to handle the possibility that the device body 1 is in a state of being moved, and if the procedure continues, the volume of blood on the electrodes of the biosensor 4 will deviate, resulting in destabilizing oxidation. Delaying time t4 to lengthen the second potential interval from time t3 to time t4 can assure enough time for stable oxidation to occur.

Step S13 is a step during which the initially set time t4 or, in the case that time t4 was modified in step S12, the modified time t4 is reached. The measurement controller 24 then directs the voltage application section 22 to end voltage application, and the voltage application section 22 promptly stops applying a voltage to the connector 5b Step S14 is a step during which the measurement controller 24 confirms whether the assessment result outputted by the motion assessment section 25 during the interval from time t3 to time t4 includes an assessment of the third state. In the case that an assessment of the third state has been included at least once, the procedure moves to step SE2. In the case that such an assessment has not been included once, the procedure moves to step S15.

Step S15 is a step during which the measurement controller 24 confirms whether the assessment result outputted by the motion assessment section 25 during the interval from time t3 to time t4 includes an assessment of the second state. In the case that an assessment of the second state has not been included once, the procedure moves to step S16. In the case that such an assessment has been included at least once, the procedure moves to step S17.

Step S16 is a step to which the procedure moves in the case that the assessment result outputted by the motion assessment section 25 was always an assessment of the first state at least during the second potential interval from time t3 to time t4. This means that motion of the device body 1 to a degree that would influence measurement of glucose concentration has not been detected.

In this case, the measurement controller 24 applies the response current outputted by the response current detector 23 at the predetermined timing during the second potential interval as the response current for specifying the glucose concentration (normal selection of response current).

In the case that the procedure has moved to steps S11 to S12, the response current is obtained at the time corresponding to time t4 before time t4 is modified, and then time t4 is modified. For example, in the case that employing the response current obtained at time t4 has been determined, the response current obtained at time t4 before it is modified is employed instead of the response current obtained at time t4 after time t4 is modified.

Step S17 is a step to which the procedure moves in the case that the assessment result outputted by the motion assessment section 25 was an assessment of the second state during the second potential interval from time t3 to time t4. This means that motion of the device body 1 to a degree that would influence measurement of glucose concentration has been detected.

Therefore, during normal selection of the response current in step S16, the precision of this response current is not guaranteed. For this reason, an additional second potential interval is started in step S17. Specifically, at time t5, the measurement controller 24 directs the voltage application section 22 to restart voltage application at a voltage level V2. The voltage application section 22 promptly restarts applying a voltage to the connector 5b.

Step S18 is a step during which time t6 has been reached. Then the measurement controller 24 directs the voltage application section 22 to end voltage application. The voltage application section 22 promptly ends applying a voltage to the connector 5b.

The time from this time t5 to time t6 is an additional second potential interval. Time t6 is set such that this additional interval is the same length as the second potential interval during time t3 to time t4.

Figure 7A:
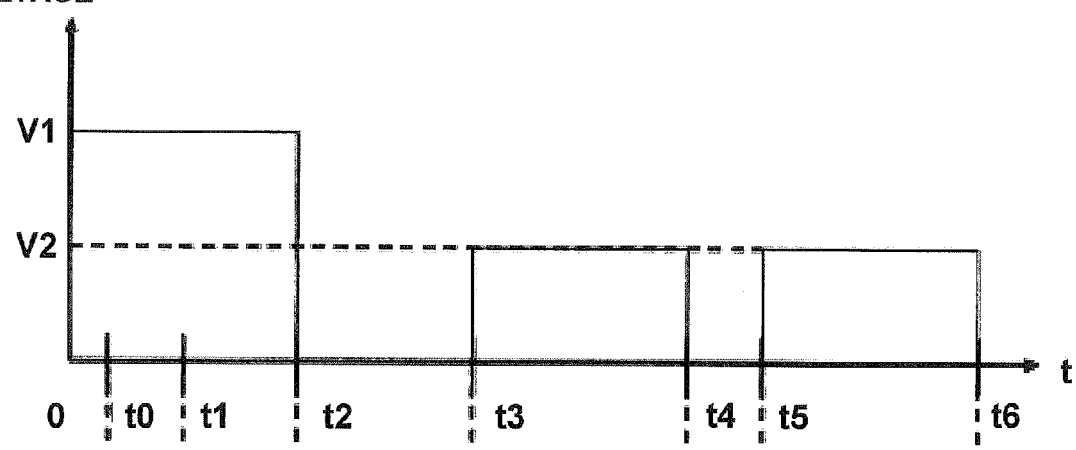
FIGS. 7A and 7B are diagrams showing the state of the application voltage and the response current in the liquid sample measuring device of FIG. 1.
Figure 7B:
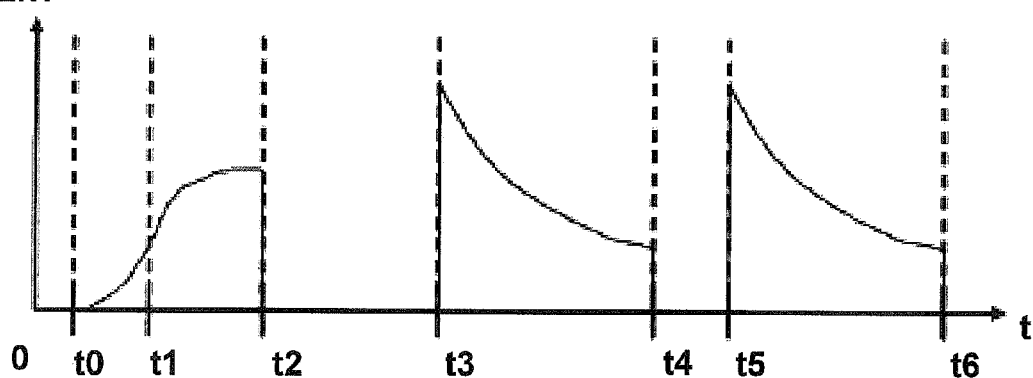

FIG. 7A is a diagram showing the state of the voltage applied to the connector 5b, and FIG. 7B is a diagram showing the state of the response current obtained from the connector 5b shown in FIGS. 5A and 5B. A voltage is applied at the voltage level V2 during time t5 to time t6, and the state of the resulting response current is tracked.

To make from time t4 to time t5 an additional waiting time, time t5 at which the additional second potential interval starts is set so that the length from time t4 to time t5 is the same as the length of the waiting time from time t2 to time t3. Alternately, time t5 may be set so that the length from time t4 to time t5 is shorter than the waiting time, as shown in FIGS. 7A and 7B.

The voltage applied during the additional second potential interval may be a voltage level V3 which differs from the voltage level V2. In this case, the additional second potential interval is called the third potential interval.

Step S19 is a step during which the measurement controller 24 confirms whether the assessment result outputted by the motion assessment section 25 during the interval from time t5 to time t6 includes an assessment of the second or third state. In the case that an assessment of the second or third state has been included at least once, the procedure moves to step SE2. In the case that an assessment of the second or third state has not been included once, the procedure moves to step S20.

Moving from step S19 to step SE2 means that intermittent or continuous motion of the device body 1 has occurred to a degree that would influence measurement of glucose concentration, selecting a response current within a range capable of guaranteeing precision is difficult even modifying conditions more than described earlier, and measurement must be repeated from the start by using another sensor.

Step S20 is a step to which the procedure moves in the case that the assessment result outputted by the motion assessment section 25 was always an assessment of the first state at least during the additional second potential interval from time t5 to time t6. This means that motion of the device body 1 to a degree that would influence measurement of glucose concentration has not been detected.

In this case, the measurement controller 24 employs the response current outputted by the response current detector 23 at the predetermined timing in the additional second potential interval as the response current for specifying the glucose concentration. That is, a selection of response current is replaced.

The relative relationship of the time from time t5 to time t6 to the timing for employing a response current at this time is the same as the relative relationship of the timing for employing a response current during the second potential interval from time t3 to time t4. For example, in the case that employing the response current outputted at time t4 is normally selected during the second potential interval from time t3 to time t4, the response current outputted at time t6 during the additional second potential interval from time t5 to time t6 is employed.

In step S21, the measurement controller 24 applies the algorithm described earlier to the response current employed in step S16 or S20 to specify the glucose concentration. The parameters and/or conditions used to compute the algorithm or the like may be the same for both the response current obtained in step S16 and the response current obtained in step S20, or different parameters and/or conditions may be set.

In other words, the additional second potential interval is set after the second potential interval to investigate beforehand whether parameters and/or conditions must be adjusted so as to correctly give the same result for the glucose concentration found on the basis of either response current. The same is true in the case that the length of the additional waiting time is modified or the voltage level applied during the additional second potential interval is modified.

Step SE1, to which the procedure moves from step S06 or step S10, and step SE2, to which the procedure moves from step S14, will be described.

Step SE1 is a step during which the current measurement of glucose concentration is deemed an error and measurement is stopped because motion of the device body 1 to a degree for which glucose concentration measurement precision cannot be compensated (the third state) was detected after dropwise dispensing was detected during the first potential interval (branch of step S06) or during the waiting interval (branch of step S10). In this case, the measurement controller 24 promptly stops measurement, and notifies the controller 10 that a measurement error has occurred.

Step SE2 is a step during which the current measurement of glucose concentration is deemed an error because motion of the device body 1 to a degree such that glucose concentration measurement precision cannot be compensated (the third state) was detected during the second potential interval, or motion of the device body 1 to a degree that would reduce reliability (the second or third state) was detected during the additional second potential interval. In this case, the controller 10 sets the result specifying the glucose concentration as a measurement error, and moves to step S22.

In step S22, the measurement controller 24 outputs the glucose concentration specified in step S21 or the measurement error set in step SE2 to the controller 10, and the controller 10 ends the operation to measure glucose concentration.

In other words, the liquid sample measuring device of the present invention has at least a first condition used for normal measurement, and a second condition which allows greater tolerance for motion of the measuring device during measurement than normally. Measurement is switched from the normal first condition to a different second condition according to the degree of motion of the measuring device detected during measurement.

The first condition corresponds to the voltage level V1 and times t2, t3, and t4 before modifying. The second condition corresponds to any of the voltage level V1 and times t2, t3, and t4 after modifying, the times t5 and t6, or a combination thereof. Switching from the first condition to the second condition is determined by the measurement controller 24 and the motion assessment section 25.

Although an example of a voltage application method (voltage application pattern) having a first potential interval, a waiting interval, a second potential interval, an additional waiting interval, and an additional second potential interval, and measuring a current profile were described in the present embodiment, the invention is not limited to this example.

For example, the voltage application pattern need not have a waiting interval. Specifically, from time t2 to time t3 may be nearly zero, and the second potential interval may be set immediately after the first potential interval. In such a case, steps S06, S07, and S08 in the flowchart of FIG. 6 may be skipped, the condition of the branch of step S10 may be switched to whether the third state occurred during times t1-t2, and the condition of the branch of step S11 may be switched to whether the second state occurred during times t1-t2.

Additionally, for example, the voltage application pattern may be to acquire a current for estimating entities in blood other than glucose during the first potential interval. For this reason, an interval for applying a voltage level required to estimate entities may be disposed during the first potential interval.

Specifically, time t1' may be disposed between time t1 and time t2, a voltage at the application voltage level V1 may be applied from time 0 to time t1 and from time t1' to time t2, a voltage at a different application voltage level from the application voltage level V1 may be applied during time t1 to time t1', and a response current may be acquired at an arbitrary time from time t1 to time t1'. In this case, the response current acquired at this time is used to calculate the glucose concentration. In this case, the flowchart of FIG. 6 is applied without changing.

Figure 6:
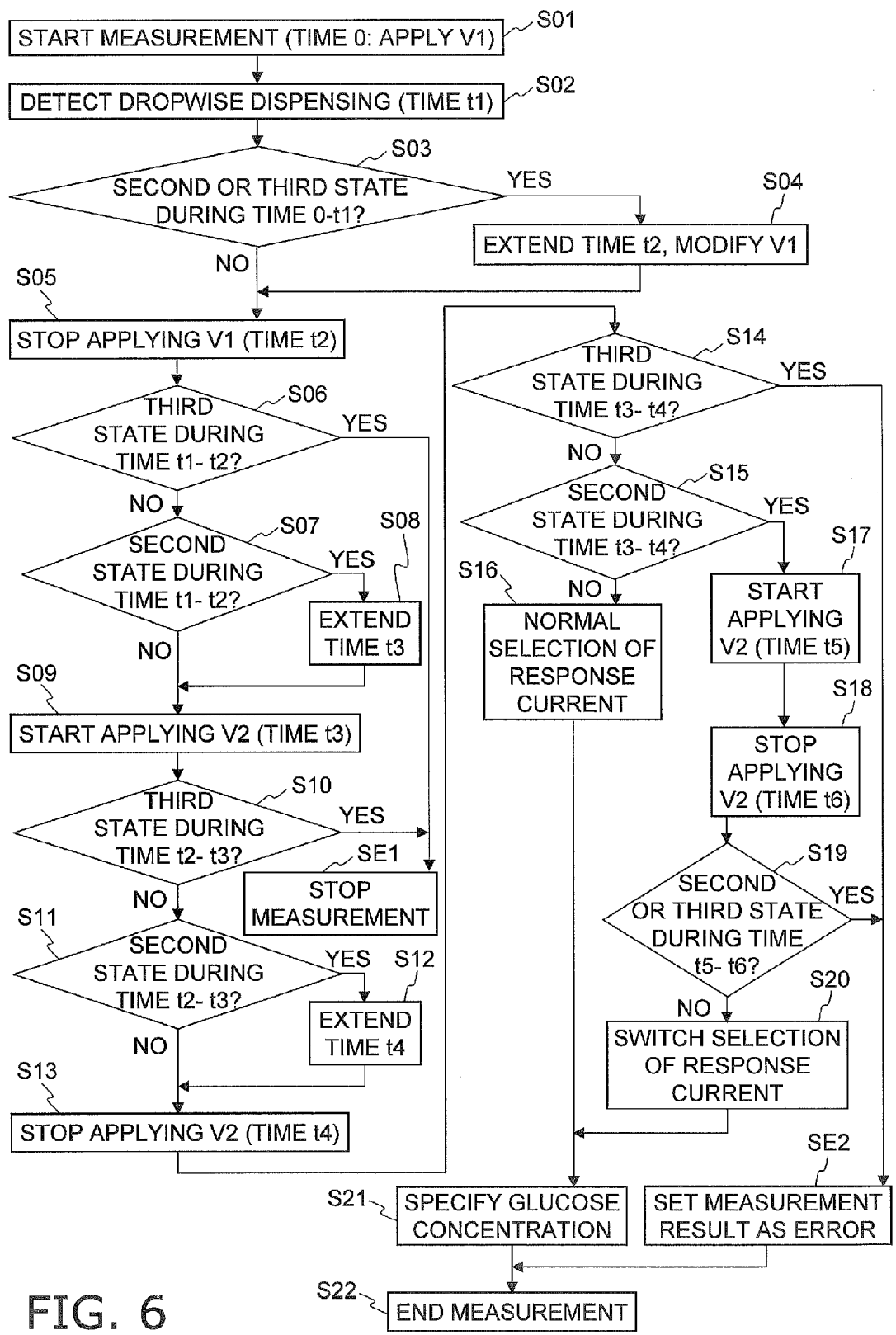
FIG. 6 is a flowchart of an operation to measure glucose concentration by the liquid sample measuring device of FIG. 1.

In other words, even if the voltage application pattern is modified, the present invention may be embodied by only modifying a portion of the flowchart of FIG. 6 as required.

As described earlier, the liquid sample measuring device of the present embodiment monitors the degree of motion of the device body 1, and continues measurement without changes, adjusts the measurement time, or adjusts so as to modify the timing of acquisition of information for specifying the glucose concentration according to the degree of this motion.

Thus, reduction of measurement precision can be prevented in the case that the measurement environment is impaired, such as by an external impact on the device body 1 while measuring glucose concentration. In other words, tolerance can be improved compared to previously in the case that motion of the device body 1 has occurred during measurement.

In particular, measurement need not be repeated by using another sensor in the case that measurement precision can be assured by adjusting the measurement time. Although previously the user had to request to puncture the patient's skin again, or had to use another biosensor because measurement routinely had to be repeated in the case that the environment was impaired during measurement, the frequency of these events can be reduced in the present invention.

Although mounting an electrochemical biosensor in the measuring device, dispensing blood of a living body in drops as the sample solution, and measuring the blood glucose concentration was described, the present invention is not limited to this usage.

An undiluted or dissolved solution of a sample essentially obtained from a living body, such as blood, urine, or interstitial fluid, may be applied as the sample solution. Alternately, a pseudo-product of these samples or a product produced by an experiment may be applied. A treatment solution of these samples which has been subjected to a pretreatment, such as denaturation or a chemical change, may be applied. The present invention may also be applied in the case that a control solution is used for the purpose of calibrating the measuring device or the like.

The present invention can be applied to any object of measurement expressed or determined in a sample, such as sugars, lactic acid, various types of cholesterol, nucleic acids, DNA, antibodies, antigens, proteins, hormones, fungi, enzymes, chemicals, antibiotics, pharmaceutical compositions, tagged markers, or chemical substances.

The biosensor may be one in which a sample solution is dispensed in drops and spread by the action of a duct, a membrane; one configured as a chamber for collecting a sample solution dispensed in drops; or the like. Alternately, instead of a biosensor, a biochip or a DNA chip may be used in which a pretreatment is carried out such as hybridizing, blood cell shrinkage, or blood cell breakdown. In other words, the present invention can be applied to all forms of sensors or chips for which there is a possibility that the position or motion of the sensor or chip may influence the measurement result from supply of a sample solution to a sensor or a chip to completion of measurement.

The method of supplying a sample solution to the biosensor is not limited to dispensing the solution in drops directly from a living body, and a sample solution may be supplied from a syringe, a cartridge, a pretreatment vessel, or the like. The object of measurement may be a cartridge or a pretreatment vessel for supplying a sample solution which has been mounted in a biosensor.

Measurement in the measuring device includes all measurement methods that can be carried out by a handheld measuring device, such as optical or magnetic methods.

INDUSTRIAL APPLICABILITY

The liquid sample measuring device according to the present invention is useful as a portable measuring device used by a user holding the device by hand.

GENERAL INTERPRETATION OF TERMS

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "forward", "rearward", "above", "downward", "vertical", "horizontal", "below" and "transverse" as well as any other similar directional terms refer to those directions of to the liquid sample measuring device. Accordingly, these terms, as utilized to describe the technology disclosed herein should be interpreted relative to the liquid sample measuring device.

The term "configured" as used herein to describe a component, section, or part of a device includes hardware and/or software that is constructed and/or programmed to carry out the desired function.

What is claimed is:

1. A liquid sample measuring device comprising:
a case on which a biosensor is detachably mounted, the biosensor configured to accept a liquid biological sample dispensed in drops on the biosensor;
a meter, disposed inside of the case, connected to the biosensor, that measures bioinformation from the liquid biological sample;
a motion measuring sensor, disposed inside of the case, that measures motion information of the case; and
controller configured to:
store at least one condition,
switch from a first condition used during normal measurement to a second condition differing from the first condition,
generate an assessment result based on a degree of motion of the case based on the motion information during measurement of the bioinformation by the meter,
measure the bioinformation based on the assessment result,
compare a variation output by the motion measuring sensor for each three-dimensional axis,
store a first threshold and a second threshold for each of the three-dimensional axes, each second threshold greater than each respective first threshold, and
generate an assessment by classifying the motion information into one of three categories of a first state, a second state, and a third state.

2. The liquid sample measuring device according to claim 1, wherein:
the controller is further configured to modify a period of time that a voltage is applied to an electrode disposed in the biosensor, from a first period of time associated with the first condition to a second period of time associated with the second condition, based on the assessment result.

3. The liquid sample measuring device according to claim 1, wherein:
the controller is further configured to modify a voltage level applied to an electrode disposed in the biosensor, from a first voltage associated with the first condition to a second voltage associated with the second condition, based on the assessment result.

4. The liquid sample measuring device according to claim 1, wherein:
the controller is further configured to modify an acquisition timing of the information acquired from a first acquisition timing associated with the first condition to a second acquisition timing associated with the second condition based on the assessment result.

5. The liquid sample measuring device according to claim 1, wherein:
the controller is further configured to change the at least one condition to the second condition based on the assessment result,
the change including changing an interval for applying a voltage to an electrode disposed in the biosensor by adding to a voltage application interval associated with the first condition.

6. The liquid sample measuring device according to claim 1, wherein:
the controller is further configured to stop measurement of the bioinformation if the assessment result of the controller indicates a degree of motion of the case to be outside of a permissible range.

7. The liquid sample measuring device according to claim 1, wherein:
the controller is further configured to assess the degree of motion of the case beginning from the time that the biosensor is mounted on the case, until measurement of the bioinformation by the meter is completed.

8. The liquid sample measuring device according to claim 1, wherein:
the controller is further configured to:
compare the variation in each of the three-dimensional axes with each respective first threshold, and
if any the variation in any of the three-dimensional axes is greater than the respective first threshold, the variation is compared in size with the respective second threshold.

9. The liquid sample measuring device according to claim 1, wherein:
the first state is associated with a normal mode wherein all of the variations are less than each of the respective first thresholds;
the second state is associated with a compensated mode of operation wherein at least one of the variations is above one of the respective first thresholds, and all of the variations are less than each of the respective second thresholds;
the third state is associated with an error mode, wherein at least one of the variations is above one of the respective second thresholds.

* * * * *